United States Patent [19]

Tahara et al.

[11] 4,357,826
[45] Nov. 9, 1982

[54] METHOD OF DETECTING PINHOLES IN HOLLOW FIBERS

[75] Inventors: Yasuteru Tahara; Kazuyoshi Koike, both of Otake, Japan

[73] Assignee: Mitsubishi Rayon Company, Ltd., Tokyo, Japan

[21] Appl. No.: 163,011

[22] Filed: Jun. 25, 1980

[30] Foreign Application Priority Data

Jul. 2, 1979 [JP] Japan .................................. 54/83737

[51] Int. Cl.³ ........................ G01N 21/89; G01M 3/38
[52] U.S. Cl. ..................................... 73/37.7; 73/160; 356/237
[58] Field of Search ................. 73/37.7, 160; 356/237, 356/238, 429, 430, 73.1

[56] References Cited

U.S. PATENT DOCUMENTS 3,240,945 3/1966 Dixon ............................. 356/429 X 4,021,217 5/1977 Bondybey et al. ................. 356/73.1

FOREIGN PATENT DOCUMENTS 2818673 11/1978 Fed. Rep. of Germany .
55-10563 1/1980 Japan .................................... 73/160

Primary Examiner—Kyle L. Howell
Assistant Examiner—Joseph W. Roskos
Attorney, Agent, or Firm—Ladas & Parry

[57] ABSTRACT

A method of and a system for detecting pinholes in hollow fibers by passing a liquid filled fiber into a zone of pressurized gas wherein the pressure of a gas is higher than that of a liquid inside the hollow fiber so that bubbles may be injected through pinholes contained in said hollow fiber and then passing the fiber through a bubble detector. The system can be operated continuously with the pinhole detector being between a device for continuously feeding the hollow fiber and a device for winding up said hollow fiber.

10 Claims, 3 Drawing Figures

METHOD OF DETECTING PINHOLES IN HOLLOW FIBERS

This invention relates to improvements in methods of detecting pinholes in hollow fibers and more particularly in semipermeable hollow fiber membranes.

Semipermeable hollow fibers in bundle assemblies are employed as permeators or filter units for many uses such as artificial organs, ultrafiltration, desalination and gas separation. When used in a permeator or filter unit, if there is present a defect such as a crack, a tear or a small hole (which can be generally called a pinhole) which passes from outside to inside of the hollow fiber, a fluid flowing outside the hollow fiber will mix directly through the pinhole with a fluid flowing inside the hollow fiber to reduce the semipermeable function. Such hollow fibers cannot be used for medical use or other uses requiring a strict semipermeability. Therefore, it is essential to inspect a permeator once produced to see if any leak is present. If some leaks are detected, the permeator will have to be repaired or disposed of as a defective product.

In Canadian Pat. No. 1031943 (1978) a method to detect and to repair leaks in a hollow fiber permeator is disclosed in which pressurised fluid for example a gas within the tubes is detected at the point of escape through a pinhole for example as a stream of bubbles in an external liquid. In order to improve the production yield of permeators, it is necessary to acquire hollow fibers having no pinhole and not to impair the hollow fibers in making permeators. It would be preferable but is difficult to product hollow fibers having no pinhole.

However, if hollow fibers are subjected to inspection to detect all pinholes before making permeators, for example, in the process of hollow fiber production and all the hollow fibers containing a pinhole are removed, it would be possible to obtain hollow fibers having substantially no pinholes. Therefore, there is a need for pinhole detecting devices which can be incorporated into the production of hollow fibers.

The object of the present invention is to provide a method of and a system for detecting the above mentioned pinholes in hollow fibers. The outside of the hollow fiber, the inside of which is filled with a liquid, is contacted with the gas having a higher pressure than that of the core liquid of the hollow fiber so that bubbles may be injected through pinholes.

According to the invention there is provided a method of detecting pinholes in hollow fibers wherein fiber is liquid filled and is subjected to gas outside the fiber which is at a pressure greater than the pressure of liquid within the fiber whereby bubbles are formed inside the fiber at the pinholes and thereafter detected.

Preferably the method is continuous in that the fiber is filled with liquid and continuously fed to the zone of higher gas pressure and after detection of any bubbles the fiber is passed through a continuous winding device.

The invention also provides a system for detecting pinholes in hollow fibers wherein there is provided a device for continuous feed of hollow fibers, a means for introducing liquid into said hollow fibers, a chamber into which said fibers are fed which chamber contains gas under a pressure higher than that of the liquid within the fiber whereby a bubble is formed at a pinhole in the fiber and a bubble detector.

The bubbles are detected by a bubble detector. Preferably the bubble detector is one utilizing a total reflection light of a boundary surface between a bubble and a core liquid. The defective hollow fibers thus detected can be eliminated by a proper means. The method of invention is preferably used in the process of hollow fiber production.

Figure 1:
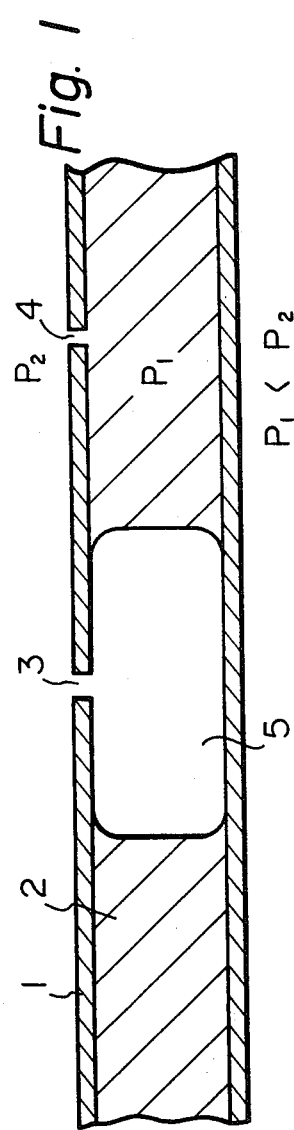
FIG. 1 is a sectioned view of a hollow fiber filled with a core liquid.
Figure 2:
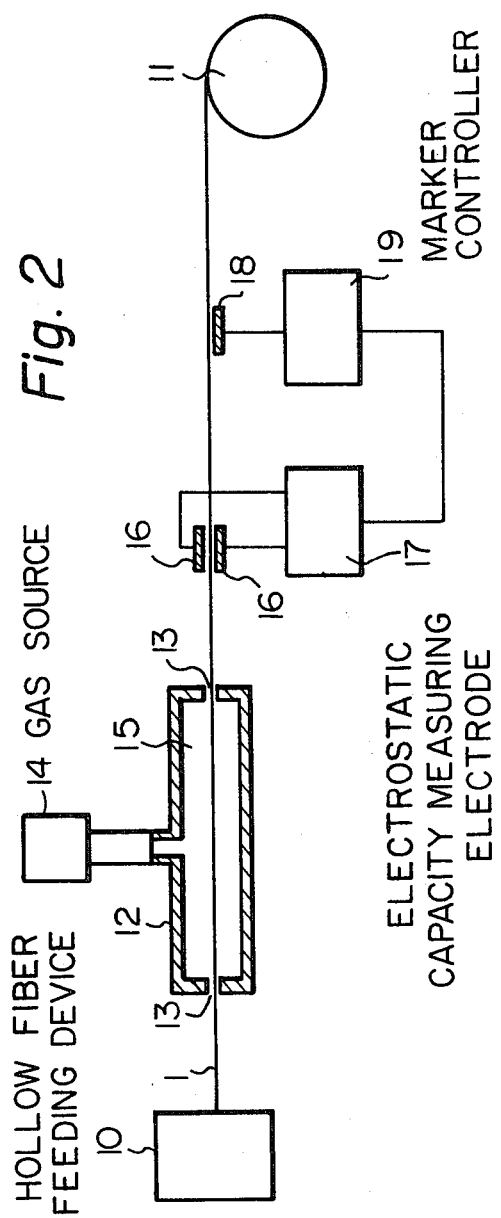
FIG. 2 is an example of a pinhole detecting device of the present invention.
Figure 3:
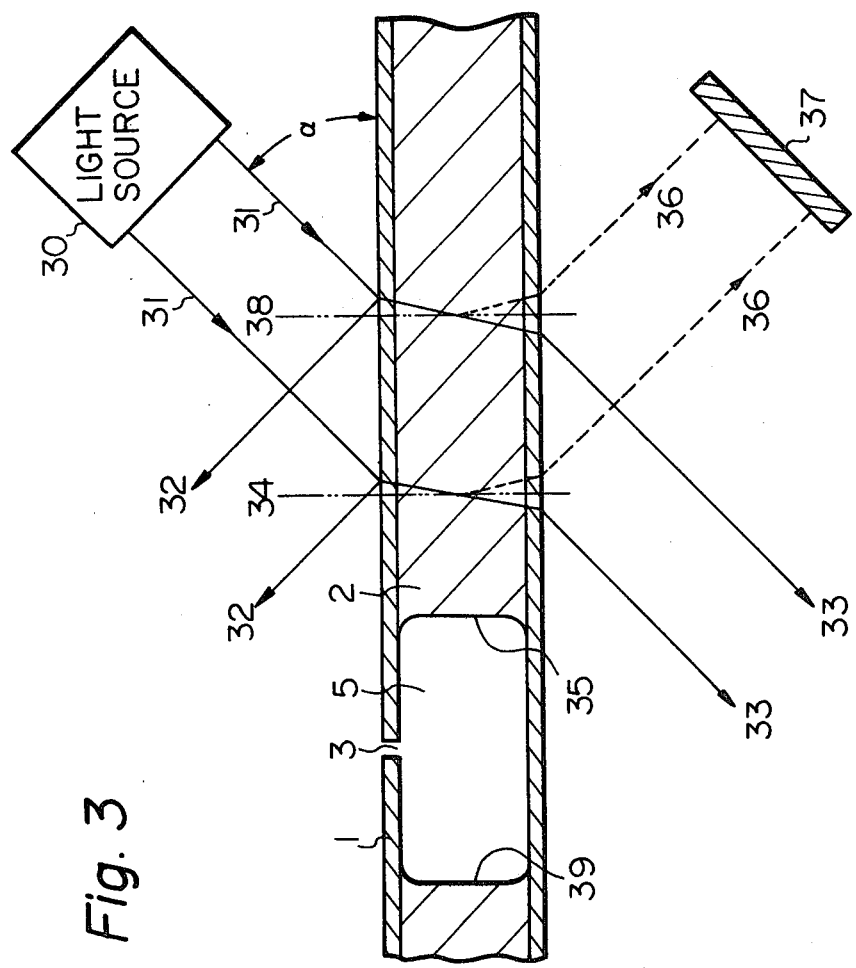
FIG. 3 is a comprehensive figure of a bubble detector utilizing a total reflection light of a boundary surface between a bubble and a core liquid.

In FIGS. 1 to 3, 1 is a hollow fiber membrane, 2 is a core liquid, 3 and 4 are pinholes, 5 is a bubble, 10 is a hollow fiber feeding device, 11 is a hollow fiber winding device, 12 is a bubble injector, 13 is a hollow fiber entry or out passage, 14 is a gas source, 15 is a gas chamber for injection of a bubble, 16 is an electrostatic capacity measuring electrode, 17 is an electrostatic capacity measuring device, 18 is a marker, 19 is a marker controller, 30 is a light source and 37 is a light detector.

The present invention will now be explained in detail. The pinhole detecting method of the present invention has the advantage that it can be applied to a hollow fiber producing step before the fibers are cut and bundled into a permeator module.

As methods of producing semipermeable hollow fibers, there are known a melt-spinning method, dry-spinning method, wet-spinning method and dry-wet-spinning method. In most cases, cores of hollow fibers obtained by the melt-spinning and dry-spinning methods are generally air filled. In applying the method of the present invention to these hollow fibers, the hollow core of the hollow fiber must be filled with a liquid in advance. If the pore size present in the porous membrane of the hollow fiber is comparatively large, a liquid will permeate into the hollow core through the porous membrane of the hollow fiber merely by dipping the hollow fiber into the liquid for a fixed time. In such case, care must be taken that no bubble should remain within the hollow fiber. If the pressure in the core of hollow fiber is reduced before the hollow fiber is dipped in a liquid, the liquid will easily permeate into the core by dipping and a hollow fiber filled with a core liquid is obtained.

On the other hand, in the case of such wet-spinning as is mentioned in the specification of Japanese Patent Specification Laid Open No. 112917/1976 and such dry-wet-spinning as is mentioned in the specification of Japanese Patent Publication No. 42883/1977, a liquid is used as a core material in the course of the hollow fiber production to maintain a circular cross-section of the fiber or to control the membrane structure and the liquid is kept inside the hollow fiber up to the final process. The method of the present invention is very conveniently applied to these hollow fibers.

The outside of the hollow fiber, the inside of which is filled with a liquid, is brought into contact with a gas such as air or nitrogen having a higher pressure than that of the core liquid. For this purpose, various methods can be employed. One method is that the hollow fiber, as wound on a bobbin, may be placed in a gas chamber, and pressurised. Another useful method for continuous operation is that the hollow fiber may be passed through a zone having a given pressure of gas. As the pressure of the core liquid is substantially near the normal pressure, it is generally enough for the gas to be at several atmospheres pressure.

When a hollow fiber is subjected to a pressurised gas as mentioned above, if a pinhole is present in the hollow fiber membrane, the gas will be injected as a bubble into the core liquid through the pinhole. The size of a bubble injected will vary depending on the size of the pinhole, the pressure difference between the core liquid and the gas and the time during which the hollow fiber is subjected to gas pressure. Therefore, by adjusting the variable factors such as the pressure of gas and the contacting time, it is possible to vary the size of bubble injected in proportion to the size of pinhole and it may be quantitatively determined in principle by a bubble detector positioned after the bubble injection. The injected bubble can be detected by suitable methods, for example, an electrical or optical method.

The present invention will be described in detail with reference to the drawings. FIG. 1 is a sectioned view of a hollow fiber filled with a core liquid. The inside of a hollow fiber 1 is filled with a core liquid 2. $P_1$ is the pressure of the core liquid and $P_2$ is the pressure of the gas in contact with the outside of the hollow fiber. When there is a pinhole 3 passing through from outside to the inside of the hollow fiber and $P_2 > P_1$, a bubble 5 will be injected. If the materials of the hollow fiber and the core liquid are specified, and the pressure difference, $P_2 - P_1$, is fixed, the volume of the bubble injected will be proportional to the size of the pinhole and the time during which the pressure difference is applied. However, in the case of a very small pinhole 4, no bubble will be injected through the pinhole due to capillary phenomena, unless the pressure difference is increased. The pressure $P_1$ of the core liquid is usually so low that, if the hollow fiber is passed at fixed velocity through a vessel of a gas having pressure high enough, a bubble will be injected into the core liquid at a pinhole.

After the injection of a bubble, it is detected by a bubble detector. The detection of a bubble is performed inside or outside of the pressure zone. In the case of a detector outside the vessel, as the pressure of the outside of a hollow fiber is reduced to normal pressure, it is necessary to detect the bubble shortly after the hollow fiber is taken out from the vessel, otherwise, the bubble vanishes from the pinhole. Thus by increasing the pressure difference or the injection time, a small pinhole not detectable by the naked eye will be magnified as converted into a bubble and it will be easily detected.

FIG. 2 is of an example of a pinhole detecting device embodying the above mentioned idea. A hollow fiber or hollow fibers 1 filled with a core liquid is continuously fed by a hollow fiber feeding device 10 and is wound up by a winding device 11. A bubble injector 12 has hollow fiber entry and exit passages 13 through which hollow fiber(s) can pass smoothly without damage. A gas source 14 comprising a compressor and a pressure regulator feeds a gas of a fixed pressure into the chamber 15 of the bubble injector to provide a zone of pressurised gas. The feed gas will leak out from the clearance between the hollow fiber and passages 13. However, if the gas fed capacity of the gas source 14 is large enough and the size of the passing holes is as small as possible, the pressure of the chamber 15 will be kept constant. Therefore when a hollow fiber having a pinhole passes through the bubble injector 12, a bubble will be injected.

A pair of electrostatic capacity measuring electrodes 16 are set near both sides of the hollow fiber 1 and connected to an electrostatic capacity measuring device 17. When the portion into which a bubble has been injected passes between the electrodes 16, the electrostatic capacity will vary and the bubble, therefore a pinhole, will be detected. The magnitude of the electrostatic capacity change will be proportional to the size of the bubble and hence it may be possible to distinguish the size of the pinhole. A marker 18 is set to mark the porton having a pinhole with an ink, paint, or paper tape and is driven by a marker controller 19 with a signal from the bubble detector.

The distance between the bubble injector 12 and the electrodes 16 of the bubble detector is desirably short and is preferably shorter than the length of the bubble injector. If this distance is too long, the bubble injected will vanish.

For the bubble detector, other methods beside the electrostatic capacity detecting method can be utilised. By radiating various electromagnetic waves such as light, infra-red rays, x-ray to the bubble, it is easy to detect the intensity of transmission, reflection, scattering, and absorbance of the electromagnetic wave.

FIG. 3 is an example of a method detecting a total reflection light caused by a boundary surface between a bubble and a core liquid. When ray 31 coming out of a light source 30 which emits a substantially parallel ray is projected at an angle $\alpha$ onto a hollow fiber 1, if there is no bubble at this position, ray 31 is divided into two rays, ray 32 and ray 33, at the surface of the hollow fiber. Ray 32 is a reflection ray and Ray 33 is a transmission ray passing through the hollow fiber and a core liquid. The angle $\alpha$ is preferably about 40 to 90 degrees in this case.

Now, if a boundary surface 35 between a bubble 5 and a core liquid 2 moves to the position of a surface 34 having a right angle to the hollow fiber, ray 33 is totally reflected on this boundary surface and the reflected ray 36 will come into a light detector 37. Until the boundary surface 35 moves to a surface 38 having right angle with the hollow fiber, the total reflection ray will continue to irradiate the light detector.

When a boundary surface 39 of the opposite side of the bubble 5, moves to the surface 34, a Fresnel reflection light will be produced at the boundary and the reflection light will also come into the light detector 37. However, the Fresnel reflection light is so much weaker than the total reflection light that it is easy to select out the total reflection light by conducting the output signal of the light detector to an amplifier and applying it to a voltage comparator.

Therefore, the bubble can be detected in the same manner as in the electrostatic capacity method.

The light source 30 is sufficient when parallel light is comparable with the light of a light emitting diode. In the case of a light source emitting a less parallel light, the allowable range of the angle $\alpha$ will be narrower. The light detector 37 is better placed in a position substantially symmetrical with the light source with respect to the hollow fiber 1. The angle $\alpha$ is set in such range that the light of the light source 30 may not directly come into the light detector 37 and that a total reflection may occur at the time when the boundary surface of the bubble passes.

Though two systems are shown as examples of a bubble detector, the present invention is not limited to the above mentioned methods. It is characterised in that a small pinhole is magnified in the form of a bubble which is easy to detect.

As explained above, pinholes in a hollow fiber filled with a core liquid can be detected without cutting or destroying the fiber. Therefore, the present invention can be used to test all fibers in the process of hollow fiber production. If the pinholes detected are removed, hollow fibers having substantially no pinholes will be obtained.

As example is shown in the following.

EXAMPLE 1

A regenerated cellulose hollow fiber containing an aliphatic acid ester as a core liquid was inspected to detect pinholes with the equipment shown in FIG. 2. The outer diameter of the hollow fiber and the thickness of the membrane were 290 micron and 20 micron. The bubble detector in FIG. 3 was used in this case.

Adjusting the pressure of the bubble injector to 3 kg/cm$^2$, a bubble about 5 mm long was detected. Inspecting the bubble portion with an optical microscope, a tear having about 20 micron in width and 100 micron in length was found.

Having now fully described the invention, it will be apparent to one of ordinary skill in the art that many changes and modifications can be made thereto without departing from the spirit or scope of the invention as set forth herein.

We claim:

1. A method of detecting pinholes in hollow fibers wherein a fiber is filled with liquid, the filled fiber is fed to a zone containing a gas outside the fiber which gas has a pressure greater than the pressure of liquid within the fiber whereby a bubble is formed inside the fiber at a pinhole and the fiber is thereafter fed to a bubble detector.

2. A method according to claim 1 wherein the hollow fibers are semipermeable fibers.

3. A method according to claim 2 wherein said fiber filled with liquid is continuously fed to a chamber containing the high gas pressure from the chamber the fiber is continuously passed to the bubble detector and after detection of any bubbles the fiber is passed to a continuous winding device.

4. A method according to claim 3 wherein that the hollow fiber is produced by a method which incorporates liquid as a core material in the fiber as produced.

5. A method according to claim 1 wherein the bubble detector detects the light reflected from a boundary surface between a bubble and the core liquid.

6. A system for detecting pinholes in hollow fibers comprising a means for introducing liquid into a hollow fiber, a feeding means to feed fiber through the system, a chamber which contains gas under a pressure higher than that of the liquid within the fiber and through which the fiber is fed by the feeding means, whereby a bubble is formed if there is a pinhole, and a bubble detector to which the fiber is fed from the chamber, for detecting such bubble.

7. A system according to claim 6 wherein the means for introducing liquid comprises a production system for hollow fibers which incorporates the liquid as a core material in the fiber as produced and which continuously feeds a fiber to the system.

8. A system according to claim 6 wherein the bubble detector is a light reflection detector which is activated by a boundary surface between a bubble and the core liquid.

9. A system according to claim 6 wherein a fiber marker which marks the fiber at the location of the pinhole is positioned after the bubble detector and activated by said detector.

10. A system according to claim 6 characterised in that a continuous winding device is located after the bubble detector to wind up said hollow fibers.

* * * * *